US010646378B2

(12) United States Patent
Gust et al.

(10) Patent No.: US 10,646,378 B2
(45) Date of Patent: May 12, 2020

(54) ABSORBENT ARTICLE HAVING A COMPOSITE WEB WITH VISUAL SIGNAL THEREON

(71) Applicant: The Procter & Gamble Company, Cincinnati, OH (US)

(72) Inventors: Kasey Marie Gust, Cincinnati, OH (US); David Christopher Oetjen, West Chester, OH (US); Christine Marie Luzader, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 708 days.

(21) Appl. No.: 15/331,955

(22) Filed: Oct. 24, 2016

(65) Prior Publication Data
US 2017/0035620 A1 Feb. 9, 2017

Related U.S. Application Data

(63) Continuation of application No. 14/057,822, filed on Oct. 18, 2013, now Pat. No. 9,492,336.

(51) Int. Cl.
| | | |
|---|---|---|
| A61F 13/15 | (2006.01) | |
| A61F 13/513 | (2006.01) | |
| B32B 27/12 | (2006.01) | |
| B32B 38/00 | (2006.01) | |
| A61F 13/84 | (2006.01) | |

(Continued)

(52) U.S. Cl.
CPC .. *A61F 13/15731* (2013.01); *A61F 13/15699* (2013.01); *A61F 13/2077* (2013.01); *A61F 13/51394* (2013.01); *A61F 13/84* (2013.01); *B32B 27/12* (2013.01); *B32B 38/145* (2013.01); *A61F 2013/15243* (2013.01); *A61F 2013/51377* (2013.01); *A61F 2013/8497* (2013.01); *B32B 37/1284* (2013.01); *B32B 37/20* (2013.01); *B32B 38/06* (2013.01); *B32B 2555/02* (2013.01)

(58) Field of Classification Search
CPC ............... A61F 13/15699; A61F 13/84; A61F 2013/8497; A61F 13/51394; A61F 2013/15243; A61F 2013/51377; A61F 13/15731; A61F 13/2077; B32B 27/12; B32B 38/145; B32B 37/1284; B32B 37/20; B32B 38/06; B32B 2555/02
See application file for complete search history.

(56) References Cited

U.S. PATENT DOCUMENTS

| | | |
|---|---|---|
| 4,623,340 A | 11/1986 | Luceri |
| 5,735,840 A | 4/1998 | Kline et al. |

(Continued)

FOREIGN PATENT DOCUMENTS

WO WO2011025486 A1 3/2011

OTHER PUBLICATIONS

Search Report and Written Opinion for PCT/US2014/060325 dated Jan. 20, 2015.

(Continued)

*Primary Examiner* — Vishal I Patel
(74) *Attorney, Agent, or Firm* — George H. Leal

(57) ABSTRACT

A process for making a composite web is disclosed. The composite web can be incorporated into an absorbent article. A volume of ink is applied to the composite web such that when the composite web is incorporated into the absorbent article, a visual signal is produced.

11 Claims, 4 Drawing Sheets

(51) Int. Cl.
    *A61F 13/20*    (2006.01)
    *B32B 37/12*    (2006.01)
    *B32B 37/20*    (2006.01)
    *B32B 38/06*    (2006.01)

(56) References Cited

U.S. PATENT DOCUMENTS

| | | |
|---|---|---|
| 7,378,130 B2 | 5/2008 | Coronado et al. |
| 7,718,844 B2 | 5/2010 | Olson |
| 7,992,994 B2 | 8/2011 | Kobayashi et al. |
| 8,142,876 B2 | 3/2012 | Ueminami et al. |
| 8,262,633 B2 | 9/2012 | Larson et al. |
| 8,292,864 B2 | 10/2012 | Hood et al. |
| 2003/0114809 A1 | 6/2003 | Gagliardi et al. |
| 2004/0170813 A1 | 9/2004 | Digiacomantonio et al. |
| 2006/0111684 A1 | 5/2006 | Berba et al. |
| 2007/0087169 A1* | 4/2007 | McFall ............ A61F 13/51496 428/172 |
| 2007/0137769 A1 | 6/2007 | Payne et al. |
| 2008/0206529 A1 | 8/2008 | Ueminami et al. |
| 2013/0178811 A1 | 7/2013 | Kikuchi et al. |

OTHER PUBLICATIONS

All Office Actions, U.S. Appl. No. 14/057,822, filed Oct. 18, 2013.

\* cited by examiner

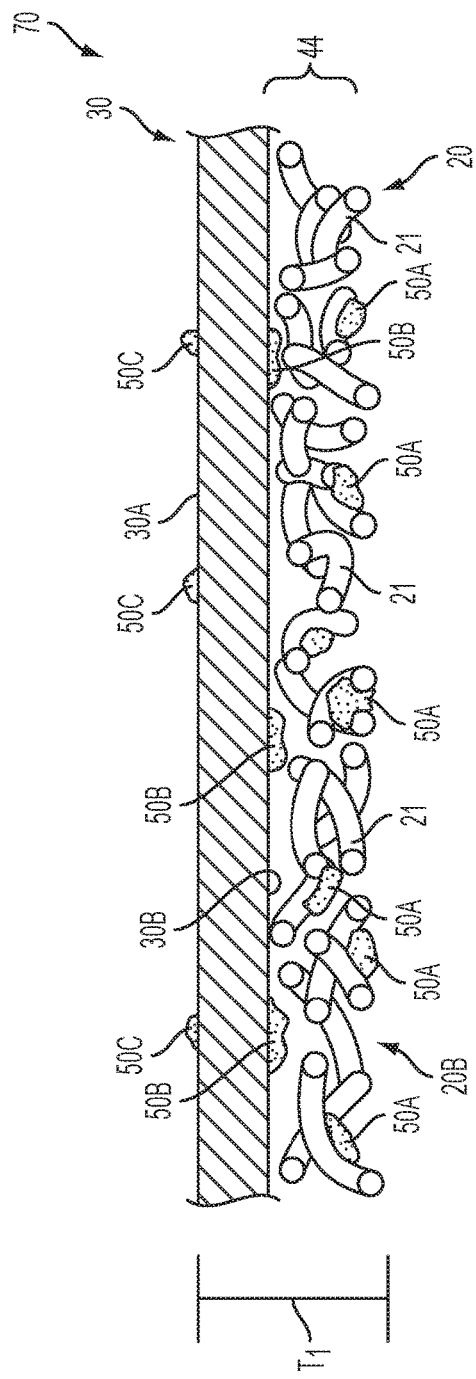
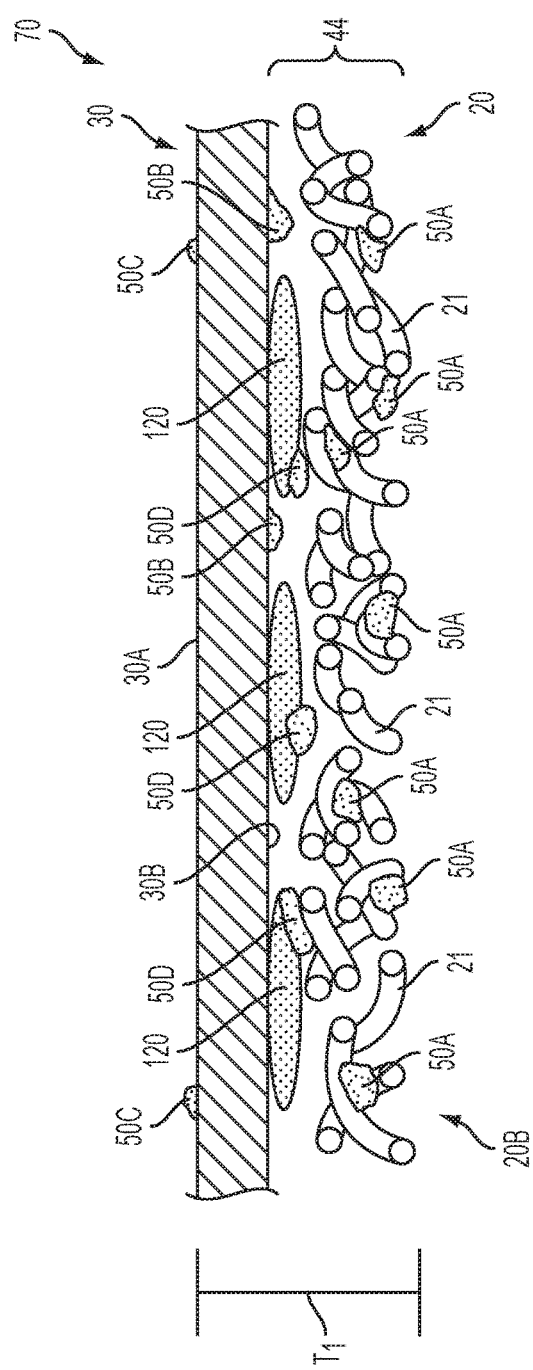

ABSORBENT ARTICLE HAVING A COMPOSITE WEB WITH VISUAL SIGNAL THEREON

FIELD

This disclosure relates to absorbent articles, and more specifically to a disposable absorbent article having an image visible on a top surface. This disclosure further relates to a process of printing on a composite web.

BACKGROUND

Absorbent articles which collect various exudates discharged from the body, such as diapers, training pants, sanitary napkins, pantiliners, interlabial devices, incontinence pads, incontinence devices, tampons, and the like, are known in the art. These absorbent articles often include one or more colored regions, graphics, designs, and the like, sometimes referred to as visual signals. Sanitary napkins and incontinence pads, for example, sometimes include a visual signal which is proximal the central portion of the absorbent article and which differs in color from portions of the absorbent article remote from the central portion of the absorbent article. Such visual signal can be produced by printing (e.g., with ink) on or below the top surface of the absorbent article. Some absorbent articles have a visual signal that is printed on one layer underlying the topsheet and visible through the topsheet. By printing on a layer below the topsheet, such as a nonwoven web, the visual signal can be viewed through the topsheet to provide for a perception of depth within the absorbent article. Creating a perception of depth within the absorbent article can reassure a user, prior to use, that during use fluid will be drawn deep inside the product and away from a user's body.

These absorbent articles often comprise at least one low-basis-weight nonwoven web. There is a need to print visual signals on these webs. However, as the basis weight of nonwoven webs upon which ink is applied decreases, the likelihood of ink blow-through during the printing process increases. Ink blow-through can be undesirable, as it can detrimentally impact manufacturing-line hygiene as well as increase manufacturing costs due to wasted ink. Additionally, the perceived quality of a visual signal produced from an image printed onto a nonwoven web may also deteriorate as the basis weight of the nonwoven web is lowered. Therefore, it is desirable to add mass to these low basis weight webs prior to printing to reduce the likelihood of ink blow-through during the printing process. With these limitations in mind, there is a continuing unaddressed need for printing a quality visual signal on a relatively low-basis-weight nonwoven web. Further, there is a continuing unaddressed need for printing a visual signal on a relatively low-basis-weight web of material while maintaining a desired level of manufacturing line hygiene and cost effectiveness. These are all goals of the present invention; embodiments described herein may achieve various combinations of these goals. A particular embodiment may, but need not, embody every goal.

SUMMARY

In an embodiment, the present disclosure is directed, in part, to a process of printing on a composite web. The process comprises the steps of providing a nonwoven layer and providing a second layer comprising a nonwoven web, an apertured film, or a combination thereof. The nonwoven layer is combined with the second layer to define a composite web. The process comprises applying a volume of ink to the composite web, where a first portion of the volume of ink is associated with the nonwoven layer and a second portion of the volume of ink is associated with the second layer. The composite web may be combined with an absorbent core and a liquid-impermeable layer to form the absorbent article.

In another embodiment, the present disclosure is directed, in part, to an absorbent article, comprising a liquid-permeable topsheet layer comprising an outer surface and an opposing inner surface, and an absorbent core. The absorbent article also comprises an intermediate layer adhered to the inner surface of the liquid-permeable topsheet layer, comprising a first surface facing the inner surface of the liquid-permeable topsheet layer, an opposing second surface, and a thickness, where an ink zone extends from the second surface of the intermediate layer through the intermediate layer and at least to the inner surface of the liquid-permeable topsheet.

In another embodiment, the present disclosure is directed, in part, to a process of manufacturing an absorbent article, comprising the steps of providing a nonwoven layer and providing a second layer comprising a nonwoven web, an apertured film, or a combination thereof. The nonwoven layer is combined with the second layer to define a composite web, the composite web having a first surface and an opposing second surface. The process also comprises applying ink to the second surface of the composite web. The composite web is combined with an absorbent core and a liquid impermeable layer to form the absorbent article. The second surface of the composite web faces the absorbent core. The ink is visible as a visual signal when viewing an outer surface of the absorbent article that is at least partially defined by the first surface of the composite web.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 4 is a cross-sectional view of a composite web subsequent to receiving ink deposits during a printing process, with the composite web comprising a secondary topsheet and a liquid-permeable topsheet.

FIG. 5 is a cross-sectional view of a composite web subsequent to receiving ink deposits during a printing process, with the composite web comprising a secondary topsheet, an adhesive layer, and a liquid-permeable topsheet.

DETAILED DESCRIPTION

Figure 1:
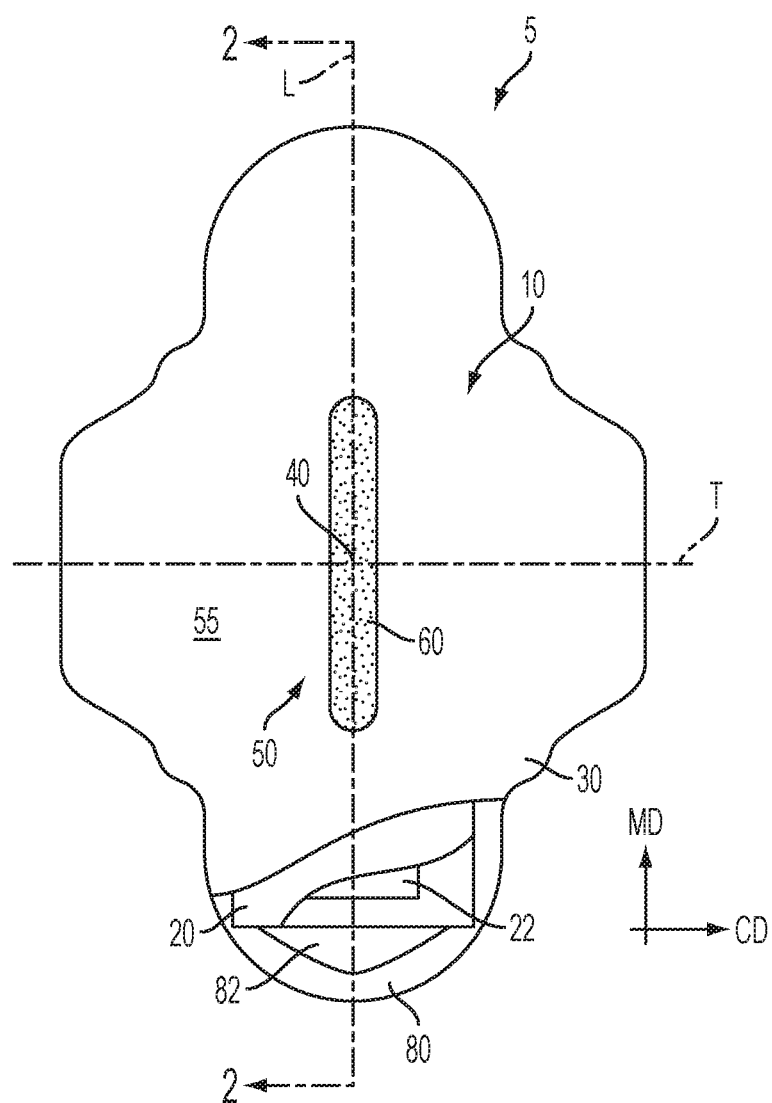
FIG. 1 is a top view of an absorbent article with some layers partially removed in accordance with a non-limiting embodiment of the present disclosure.

Various non-limiting embodiments of the present disclosure will now be described to provide an overall understanding of the principles of printing a visual signal on a composite web. One or more examples of these non-limiting embodiments are illustrated in the accompanying drawings. Those of ordinary skill in the art will understand that the printable composite webs described herein and illustrated in the accompanying drawings are non-limiting embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

A process has been discovered for first combining two webs into a composite web, and then printing on the second surface of one web such that a resultant visual signal is visible from the first surface of the other web. Thus, a printable composite web, and method and apparatus for printing on a composite web are disclosed. The composite web can comprise various types of material layers, including one or more nonwoven layers. A nonwoven layer can be combined with another nonwoven web, a formed film (e.g., an apertured film), or combinations thereof, to form the composite web. The composite web can be incorporated into an absorbent article, with one layer of the composite web functioning as a topsheet, for example, and another layer of the composite web functioning as a secondary topsheet, or other component of the absorbent article. Or, both layers of the composite web may function as a composite topsheet, which in turn may be combined with a separate secondary topsheet. While a variety of materials can be incorporated into the composite web, in certain embodiments, the nonwoven layer can have a basis weight ranging from about 8 grams per square meter (gsm) to about 55 gsm.

Air permeability (or porosity) is used herein as a way to measure how easy it is for ink to pass through a material. A high air permeability number generally means air (and thus ink) can easily penetrate through the material. Low-basis-weight materials typically have high air permeability as there isn't a lot of material to block the air. As air permeability increases, so does the potential for ink blow-through. Accordingly, to achieve a good quality printed image with limited blow-through, it is desirable to print onto a material having low air permeability combined with a closed (vs open) molecular structure. It is advantageous to print to a composite web versus printing simply to one layer, as combining two layers of material helps create a closed structure with low air permeability. For embodiments incorporating a formed film in the composite web, the formed film, can be, for example, a macroscopically-expanded, three-dimensional, fluid-pervious, polymeric web. In certain embodiments, the formed film can have an air permeability of at least about 200 cubic ft. per minute (cfm) per sq. ft, or at least about 300 cfm per sq. ft., or at least about 400 cfm per sq. ft., or at least about 500 cfm per sq. ft, or at least about 600 cfm per sq. ft. For embodiments incorporating a higher basis-weight nonwoven in the composite web, the air permeability of the composite web may be lower than 300 cfm per sq. ft.

Introduction

"Absorbent article", as used herein, refers to disposable devices such as infant, child, or adult diapers, pant-style diapers, training pants, sanitary napkins, pantiliners, incontinence pads, diaper inserts, and the like which are placed against or in proximity to the body of the wearer to absorb and contain the various exudates discharged from the body. Typically, these articles comprise a topsheet, backsheet, an absorbent core, and optionally other components, with the absorbent core normally placed at least partially between the backsheet and the topsheet. The absorbent articles of the present disclosure will be further illustrated in the below description and in the Figures in the form of a sanitary napkin. Nothing in this description should be, however, considered limiting the scope of the claims. As such, the present disclosure applies to any suitable form of absorbent articles (e.g., training pants, adult incontinence products, diapers, and so forth).

"Absorbent core", as used herein, refers to a structure typically disposed between a topsheet and backsheet of an absorbent article for absorbing and containing liquid received by the absorbent article. The absorbent core can comprise one or more substrate layers, an absorbent material disposed on the one or more substrate layers, and a thermoplastic adhesive composition on the absorbent material. The thermoplastic adhesive composition can be on the absorbent material and at least a portion of the one or more substrate layers. The absorbent core does not include an acquisition system, a topsheet, or a backsheet of the absorbent article. In a certain embodiment, the absorbent core would consist essentially of the one or more substrate layers, the absorbent material, the thermoplastic adhesive composition, and optionally a cover layer.

"Nonwoven web", as used herein, means a manufactured sheet, web, or batt of directionally or randomly orientated fibers, bonded by friction, and/or cohesion, and/or adhesion, excluding paper and products which are woven, knitted, stitch-bonded incorporating binding yarns or filaments, or felted by wet-milling, whether or not additionally needled. The fibers can be of natural or man-made origin and can be staple or continuous filaments or be formed in situ. Commercially available fibers can have diameters ranging from less than about 0.001 mm to more than about 0.2 mm and can come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter (g/m2 or gsm).

"Joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

General Description of an Absorbent Article

Figure 2:
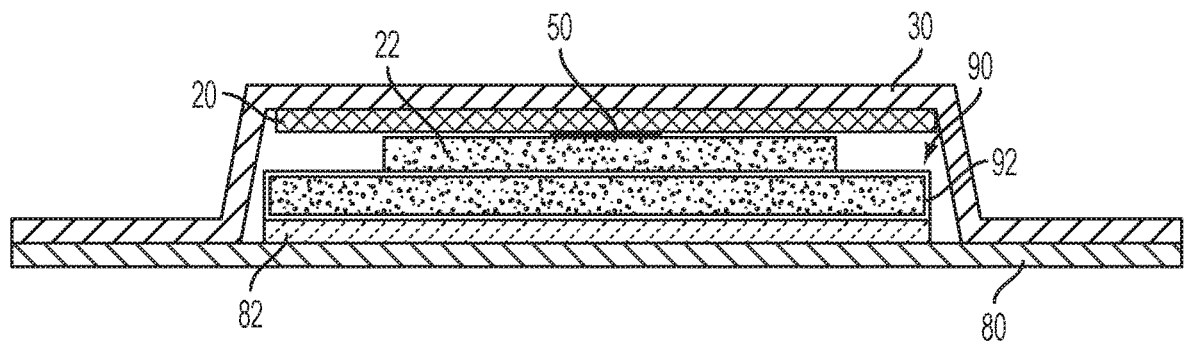
FIG. 2 is a cross-sectional view of the absorbent article taken about line 2-2 of FIG. 1 in accordance with a non-limiting embodiment of the present disclosure.
Figure 3:
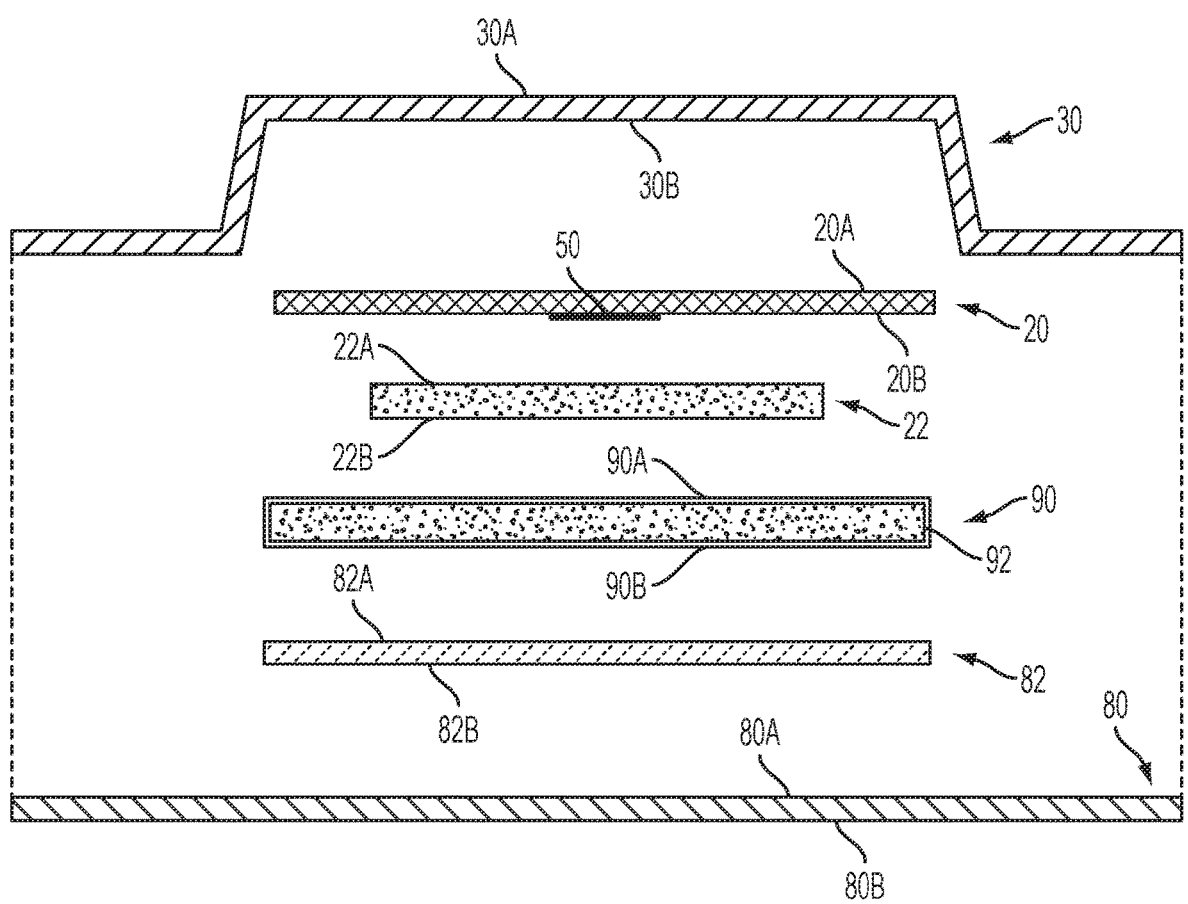
FIG. 3 is an exploded cross-sectional view of the absorbent article of FIG. 2.

An example absorbent article 5 according to the present disclosure, shown in the form of a sanitary napkin, is represented in FIGS. 1-3. This type of absorbent article is shown for illustration purpose only as the present disclosure can be used for making a wide variety of other absorbent articles. FIG. 1 is a top view of the example absorbent article 5, in a flat-out state, with portions of the structure being cut-away to more clearly show the construction of the absorbent article 5. FIG. 2 is a cross-sectional view of the absorbent article of FIG. 1 taken along line 2-2, while FIG. 3 is an exploded cross-sectional view of the absorbent article of FIG. 2.

Referring to FIG. 1, the absorbent article 5 can have a substantially planar configuration and a centroid 40. The centroid 40 is the in-plane center of mass of the absorbent article 5. The centroid 40 is at the intersection between the longitudinal centerline L and transverse centerline T. The transverse centerline T is orthogonal to the longitudinal centerline L. The absorbent article 5 can, but need not be, symmetric about the transverse centerline T. The absorbent article 5 has a body-facing surface 10 and a garment facing surface (not shown).

Referring to FIGS. 1-3, the absorbent article 5 comprises a plurality of layers to promote certain liquid handling behaviors. Example layers include a liquid-permeable topsheet 30 and an absorbent core 90. Some embodiments can also include a top core 22, as illustrated. The absorbent core 90 can have a number of suitable arrangements, for example the absorbent core 90 can have a tissue outer wrapping 92 (FIG. 3). The absorbent articles can also have a backing material 82 and a backsheet 80.

To help ensure that fluids flow into the absorbent core 90, some absorbent articles are constructed with what is sometimes referred to as a secondary topsheet 20 (STS) positioned intermediate the topsheet 30 and the absorbent core 90. This secondary topsheet 20 is designed to acquire the fluid on the liquid-permeable topsheet 30 and distribute it to the underlying absorbent core 90. To help ensure that the secondary topsheet 20 transfers the fluid to the absorbent core 90, the secondary topsheet 20 can have sufficient capillarity to draw the fluid through the liquid-permeable topsheet 30. To ensure that the fluid flow continues onto the absorbent core 90, the secondary topsheet 20 can be designed with more permeability than the absorbent core 90, and less capillarity than the absorbent core 90. A secondary topsheet can be an airlaid-tissue web made from hydrophilic cellulosic fibers, sometimes referred to as an airlaid STS. Such secondary topsheets, however, cannot typically be fusion bonded to a liquid-permeable topsheet due to the use of plain cellulosic fibers in the web. Accordingly, an adhesive can be used during the manufacturing process as a bonding agent between the airlaid STS and the liquid-permeable topsheet. If fusion bonding is desired, a polyethylene (PE) powder can be incorporated into the airlaid STS.

As shown in FIG. 3, each of the layers of the absorbent article 5 have a first surface (shown as 30A, 20A, 22A, 90A, 82A and 80A) and an opposing second surface (shown as 30B, 20B, 22B, 90B, 82B and 80B). The first surfaces 30A, 20A, 22A, 90A, 82A and 80A, or at least portions thereof, are generally oriented to be body-facing, or wearer-facing, and the second surfaces 30B, 20B, 22B, 90B, 82B and 80B, or at least portions thereof, are generally oriented to be garment-facing when the absorbent article 5 is in a flat-out state.

The absorbent article 5 can be considered to have a viewing surface that is the body-facing surface 10 (FIG. 1). The body-facing surface 10 can be the side of the absorbent article 5 that is in contact with the wearer's body when the absorbent article 5 is worn, as might be the case for a sanitary napkin, pantiliner, or adult incontinence product, or is inserted into the wearer's body, as might be the case for a tampon. For a generally cylindrical tampon, the longitudinal centerline L is considered to be on the body-facing surface 10 of the tampon, aligned with the central axis of the tampon and the centroid 40 can be the midpoint of the longitudinal centerline L.

When creating an absorbent article, such as a sanitary napkin, having a visual signal, it is desirable to add ink to a surface other than the body-facing surface of the article (e.g., first surface 30A of the topsheet 30); doing so minimizes the chance of wearer irritation from the ink, maintains the aesthetic clarity of the visual signal, or the like. Some current absorbent articles comprise a secondary topsheet which is printed on its first (body-facing) surface and then combined with a second layer, such as a topsheet. Other current absorbent articles comprise a topsheet which has been printed (e.g., with a flexographic printer) on its second (garment-facing) surface and then combined with a second layer, such as a secondary topsheet. The second surface 20B of the secondary topsheet 20 can have ink, paint or other type of colorant printed thereon. In the illustrated embodiment, ink deposits 50 are printed onto the second surface 20B. The ink deposits 50 can be any colorant suitable for deposition onto a nonwoven web, including water-based inks or dyes, solvent-based inks or dyes, phase transition inks (e.g., wax-based inks which are solid at room temperature and must be melted to print), UV-curable inks or dyes, paint, pigment, or liquid colorants such as food coloring. The ink deposits 50 can produce a color contrasting with the color of the secondary topsheet 20 and the liquid-permeable topsheet 30 and can be, for example, primary colors and common colors such as red, green, blue, yellow, pink, purple, orange, or black. If the secondary topsheet 20 and/or the liquid-permeable topsheet 30 is dark a color, colorant can be light colors such as light gray, silver, white, or beige. The ink deposits 50 may be the same color as the liquid-permeable topsheet 30 or secondary topsheet 20, but in a different hue such that there is a noticeable contrast, such as a light blue topsheet and a vivid blue ink deposit. While the present discussion is generally directed to inks applied to an absorbent article to yield a deliberate visual signal, the process herein may also be used to apply another substance (either having color or being generally colorless), such as an adhesive, non-contact perfume, etc. to an inner layer of an absorbent article. Further, the ink or other substance deposited need not form a visual signal to reap the benefits.

It is common in the industry to print on the first surface of a secondary topsheet and then combine it with a second layer, such as a liquid-permeable topsheet; this yields a composite web with a visual signal likely viewable from the first surface of the secondary topsheet. But, this process can have disadvantages, such as a high level of ink blow-through from printing to open, highly porous individual layers. A process has been discovered for first combining two webs into a composite web, and then printing on the second surface of one web such that the resultant visual signal is visible from the first surface of the other web. Ink deposits 50 on the second surface 20B of the secondary topsheet 20 can be applied after the secondary topsheet 20 has been combined with a second layer, such as the liquid-permeable topsheet 30. In some cases, the secondary topsheet 20 in combination with a second layer is referred to as a composite web 70 (FIGS. 4, 5, 6 and 7), as described in more detail below.

Exemplary printing processes for applying the ink deposits 50 include digital printing (e.g., with inkjet or laser printers), gravure printing and flexographic printing. Other printing processes as are known in the art can be used, each with various advantages and disadvantages. One advantage of printing via a flexographic printing process is that the nip setting at the printing stage can be adjusted and set such that only the second surface 20B of the secondary topsheet 20 contacts the inked roll in a highly controllable manner.

However, there are many advantages of digital printing over flexographic printing: flexibility, smaller footprint, operability, more automated, color response is not dependent on operator settings (e.g., not dependent on the nip setting as with flexographic printing since the desired color saturation is in the image file that is loaded into the digital printer). Thus, the preferred method of applying the ink deposits 50 is digital printing.

Yet, digital printing such as continuous inkjet printing can result in ink passing through the layers of a web due to the high drop speed (more so than may be seen with piezo/drop-on-demand or flexographic printing). So, ink blow-through is more of a problem when printing digitally than it is with other common printing methods. It has been found that digital printing on a composite formed film and low basis weight nonwoven or composite nonwoven/nonwoven web results in improved image quality over single web printing because more ink stays on the composite web because of higher combined basis weight than printing on single web. Digital printing onto a composite web also decreases the amount of blow through; more ink stays on the composite web because of higher combined basis weight than printing on single web. Further, digital printing onto a composite web enables high visual signal quality with online printing, but with low-cost, low-basis weight materials.

The ink deposits 50 deposited on the second surface 20B of the secondary topsheet 20 produce a visual signal 60 (FIG. 1) that is at least partially visible (can be visually perceived by the observer) through the body-facing surface 10. The visual signal 60 is visible when the body-facing surface 10 is presented towards an observer even though liquid-permeable topsheet 30 is between the observer and the secondary topsheet 20. It is possible to control the ink penetration such that ink is deposited on more layers than just the secondary topsheet. In some cases, the visual signal 60 is produced not only by ink deposits 50 applied to the second surface 20B of the secondary topsheet 20 but also by ink deposits 50 that reached (e.g., via capillary action) the second surface 30B of the liquid-permeable topsheet 30 when the ink was applied to the composite web 70 during the printing process. Accordingly, it is possible to print on multiple layers during the same printing step.

Referring to FIG. 1, when the body-facing surface 10 of the absorbent article 5 is viewed, the absorbent article 5 can have a background region 55. The background region 55 is a region that is visually distinguishable from the visual signal 60. The background region 55 can be white or any other color visually distinguishable from the visual signal 60. Generally, the visual signal 60 can render a perception of depth to the absorbent article 5 and in some cases provide guidance for alignment. Further, one or more visual signals 60 can communicate various functions of portions of absorbent article 5, for instance, such portions of the absorbent article 5 that might act or be perceived to act as a barrier to flow of liquids. The visual signal 60 can be coincident with the centroid 40, for instance when the centroid 40 is the in-plane center of mass of the absorbent article 5, thereby showing the user the location of the absorbent article 5 that should be proximal her vaginal opening or urethra. Designs in which the visual signal 60 is symmetric about the longitudinal centerline can provide for a more pleasing impression of the absorbent article 5. The visual signal 60 may comprise one continuous shape, such as a peanut or flower, or it may be comprised of multiple smaller shapes which, taken together, form a graphic, design, or pattern.

Ink deposits 50 can be closely spaced so as to form a substantially complete coverage of the second surface 20B of the secondary topsheet 20, they can be spaced relatively far apart, or they can be appropriately spaced to form a desired shape, pattern, or graphic image, such as an oval or rectangle, for example. The ink deposits 50 can be coincident with the longitudinal centerline L, that is, a portion of the ink deposits 50 can intersect with the longitudinal centerline L. Furthermore, the ink deposits 50 can include a plurality of different colors to create the desired visual signal 60 that is visible through the body facing surface 10. In one embodiment, ink deposits 50 are colorfast so that they do not dissolve, degrade, or run when insulted with at least one of water, urine, or menses. In another embodiment, ink deposits 50 can be soluble in at least one of water, urine, or menses, such that upon liquid insult the imprinted color changes or disappears. Such color change can indicate wetness, volume of fluid, position of fluid, and/or type of fluid. The shape, size, coloration, placement, and intensity of the ink deposits 50 and resulting visual signal 60 can be varied in ways limited only by the size of the substrate and the printing techniques employed. For example, by use of letter press, lithographic, screen printing, flexographic or gravure printing techniques, virtually any graphic in any color or color combination can be rendered on the second surface 20B of the secondary topsheet 20. Moreover, by adjusting processing variables such as the nip between rollers in a flexographic process, the amount of ink and the position of ink can be varied to give various impressions of color intensity, brightness/darkness, hue, saturation, and depth perception.

FIG. 4 is a cross-sectional view of a composite web 70 subsequent to receiving ink deposits during a printing process. The composite web 70 comprises the secondary topsheet 20 and the liquid-permeable topsheet 30. The secondary topsheet 20 is a nonwoven web having a plurality of fibers 21 and can have any suitable basis weight. In some embodiments, for example, the secondary topsheet 20 has a relatively low basis weight ranging from about 8 grams per square meter (gsm) to about 70 gsm. In some embodiments, for example, the secondary topsheet 20 has a basis weight ranging from about 10 gsm to about 55 gsm. In some embodiments, for example, the secondary topsheet 20 has a basis weight ranging from about 15 gsm to about 40 gsm. In some embodiments, for example, the secondary topsheet 20 has a basis weight less than about 50 gsm. Additionally, pores of the secondary topsheet 20 range in size from about 10 microns to about 200 microns. In some embodiments, the pores range in size from about 50 microns to about 100 microns. While the liquid-permeable topsheet 30 in FIG. 4 is illustrated as a formed film, the liquid-permeable topsheet 30 can be any suitable type of material layer, such as a nonwoven web, an apertured film, or a combination thereof. The liquid-permeable topsheet 30 can have an air permeability of at least about 300 cubic ft. per minute (cfm) per sq. ft. The composite web 70 can have a total thickness, or caliper (per ASTM D645), shown as $T_1$, from about 120 μm to about 1.3 mm; $T_1$ depends on the different layers combined to create the composite web. In some embodiments, composite web 70 can be less than about 120 μm or more than about 1.3 mm.

The application of ink to the second surface 20B of the secondary topsheet 20 during the printing process results in a first volume, or portion, of ink 50A associated with the fibers 21 of the secondary topsheet 20 and a second volume, or portion, of ink 50B that reaches the second surface 30B of the liquid-permeable topsheet 30. Additionally, a third volume, or portion, of ink 50C may pass through the liquid-permeable topsheet 30 during the printing process. The third portion of ink 50C may be referred to as ink blow-through. Despite the relatively low basis weight of the secondary topsheet 20, the amount of ink blow-through 50C can still be relatively low due to the joining of the secondary topsheet 20 with the liquid-permeable topsheet 30 prior to the application of the ink. Providing another substrate (e.g., the top sheet) for the ink to adhere to besides simply the secondary topsheet creates a higher mass composite and thus a more tortuous path for the ink to pass through. Accordingly, manufacturing line hygiene may not be as detrimentally impacted as compared to other methods for printing solely on low basis weight materials vs higher basis weight composites. This also improves the clarity of the image printed as compared to an image printed solely on low basis weight materials.

In one embodiment, an intermediate layer is adhered to the inner surface of the liquid-permeable topsheet layer to form a composite web; the intermediate layer comprises a first surface facing the inner surface of the liquid-permeable topsheet layer, an opposing second surface, and a thickness. An ink zone extends from the second surface of the intermediate layer through the intermediate layer and at least to the inner surface of the liquid-permeable topsheet. This yields a composite web with ink present on more than one layer. In traditional printing processes, wherein layers are first printed and then combined, the ink applied to one or both layers is dry prior to the combination and doesn't transfer to the other layer. So, the instant process is useful for printing to multiple layers with one only printing step.

As shown in FIG. 5, the composite web 70 can include one or more additional layers, such as an adhesive layer 120. In the illustrated embodiment, the adhesive layer 120 bonds the first surface 20A of the secondary topsheet 20 to the second surface 30B of the liquid-permeable topsheet 30. The adhesive layer 120 can be applied to either or both of the liquid-permeable topsheet 30 and the secondary topsheet 20 during the manufacturing process. Since the adhesive layer 120 is present when ink is deposited onto the composite web 70, a volume of ink can be associated with the adhesive layer 120, which is illustrated as a fourth volume, or portion, of ink 50D.

The composite web 70 can have an ink zone 44 which extends from the second surface 20B of the secondary topsheet 20, through the secondary topsheet 20, and at least to the second surface 30B of the liquid-permeable topsheet 30. For composite webs 70 having an adhesive layer 120, as shown in FIG. 5, the ink zone 44 can extend from the second surface 20B of the secondary topsheet 20, through the secondary topsheet 20, through the adhesive layer 120, and at least to the second surface 30B of the liquid-permeable topsheet 30. Further, while FIGS. 4 and 5 illustrate at least a portion of ink associated with each layer of the composite web 70, this disclosure is not so limited. In fact, in some embodiments, ink may only be associated with the secondary topsheet 20 and not reach the liquid-permeable topsheet 30.

The volume of ink associated with the secondary topsheet 20 (shown as the first portion of ink 50A) may be about 30% to about 90% of the total volume of ink applied to the composite web 70 at one time (e.g., at one printing unit with one or more print heads). Additional volumes of ink may be applied to the individual layers making up the composite web prior to combination, to the composite web alone, or to the composite web after combination with additional layers in additional printing steps or units. The volume of ink associated with the liquid-permeable topsheet 30 (shown as the second portion of ink 50B) may be about 10% to about 70% of the total volume of ink applied to the composite web 70 during the printing process. In some embodiments, the volume of ink that is blown through the composite web 70 during the printing process (shown as the third portion of ink 50C) can be less than about 10%, or less than about 5%, of the total volume of ink applied to the composite web 70 during the printing process. This low level of ink that is blown through the composite web with the current process is advantageous in comparison to prior art means of printing on a low basis weight secondary topsheet, for instance, due to line hygiene, cost due to lost ink, and cost to clean wasted ink. For composite webs 70 having an adhesive layer 120 (FIG. 5), the volume of ink associated with the adhesive layer 120 (shown as the fourth portion of ink 50D) may be about 1% to about 70% of the total volume of ink applied to the composite web 70 during the printing process.

The ink deposited within the ink zone 44 of the composite web 70 produces the desired visual signal 60 (FIG. 1). The visual signal 60 can have an L* value of about +30 to about +90 in the CIE 1976 (L*a*b*) color space, as measured at the outer, or body-facing, surface 10 of the absorbent article 5. In some embodiments, the visual signal 60 can have an L* value of about +40 to about +70 in the CIE 1976 (L*a*b*) color space, as measured at the outer surface of the absorbent article 5. The L* value can be measured using a Hunter Labscan XE 45/0 geometry reflectance spectrophotometer. Technical description of the system can be found in an article by R. S. Hunter, 'photoelectric color difference Meter', Journal of the Optical Society of America, Vol. 48, pp. 985-95, 1958. Devices that are specially designed for the measurement of color on the Hunter scales are described in U.S. Pat. No. 3,003,388 to Hunter et al., issued Oct. 10, 1961. Further, it has been found that printing on a nonwoven layer of a composite web 70 that has a relatively low basis weight produces a darker visual signal 60 (FIG. 1) than a visual signal generated by printing solely on the nonwoven layer prior to combining it with a topsheet layer. Darker visual signals 60 are perceived by consumers as conveying a higher quality image and/or absorbent article. In some cases, the darkness of the visual signal 60 is comparable to the darkness of other visual signals that are printed onto substrates having higher basis weights.

General Description of a Process for Printing on a Composite Web

Figure 6:
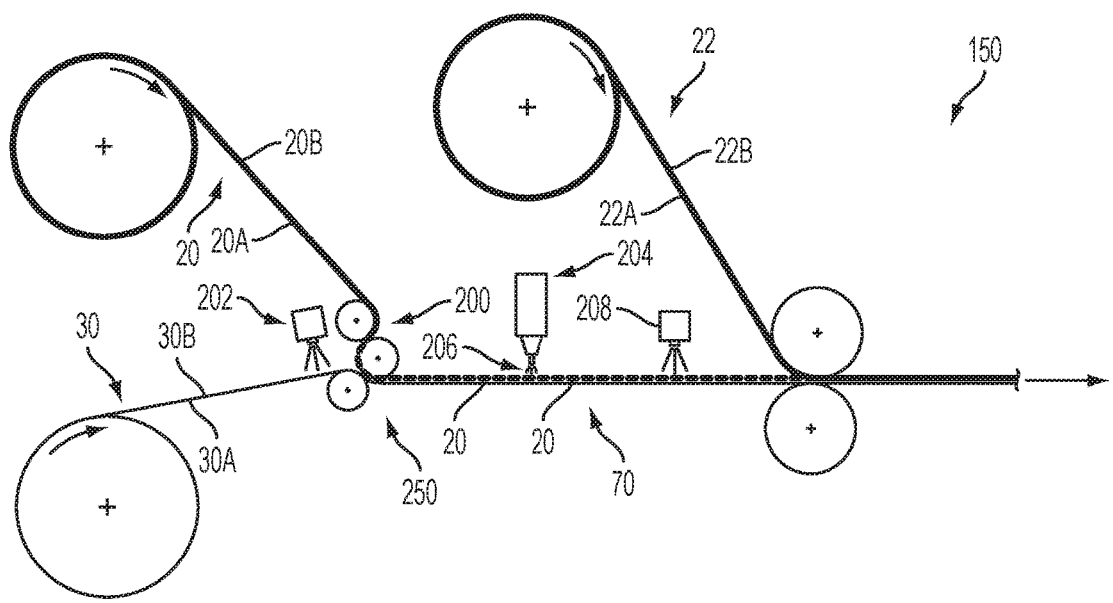
FIG. 6 is a schematic side view of a process for producing a composite web and then printing onto the composite web in accordance with one non-limiting embodiment.
Figure 7:
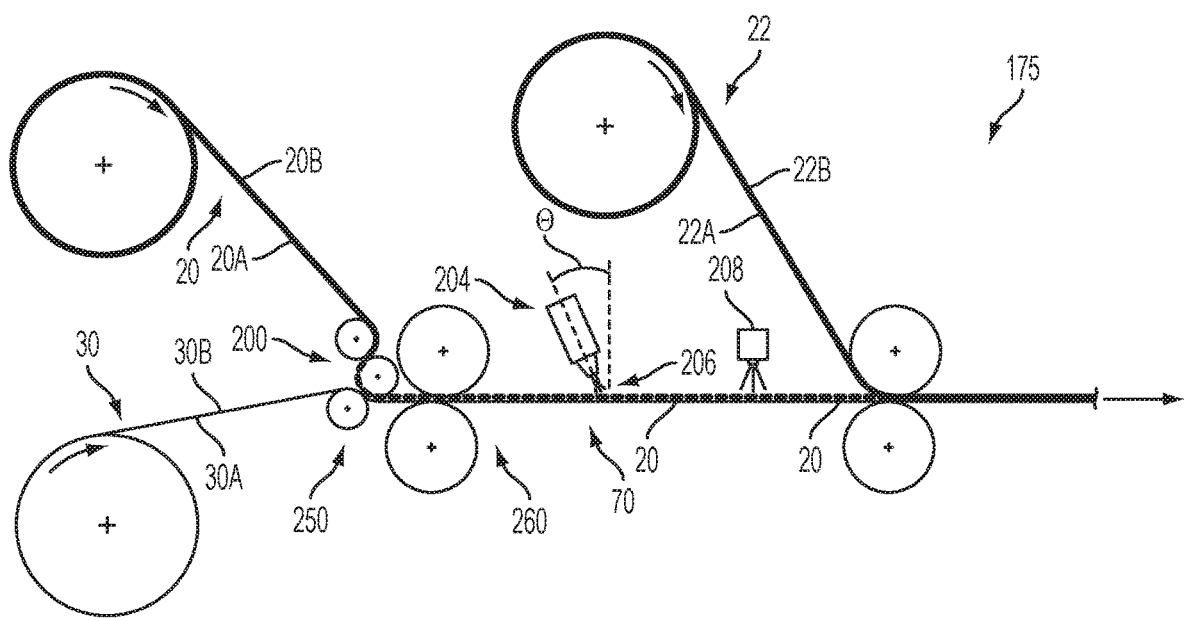
FIG. 7 is a schematic side view of a process for producing a composite web and then printing onto the composite web in accordance with one non-limiting embodiment.

FIG. 6 is a schematic side view of a process 150 for making and printing on a composite web 70 in accordance with one non-limiting embodiment. The liquid-permeable topsheet 30 and the secondary topsheet 20 are provided from storage rolls or from other parts of the manufacturing process. The secondary topsheet 20 is directed past an adhesive coater 202 which delivers an adhesive layer 120 (FIG. 5) to the secondary topsheet 20. The adhesive coater 202 can be a contact-type applicator or a non-contacting applicator. Additionally, it should be noted that the adhesive coater 202 can be replaced by another device for applying joining means to either the secondary topsheet 20 or the liquid-permeable topsheet 30. Such may be the case if alternative bonding means are being used such as ultrasound, heat, pressure or the like. The secondary topsheet 20 is then sent to a cut-and-slip unit 200, a cut-and-lay unit (not shown), or other device, as is known in the art. The liquid-permeable topsheet 30 and the secondary topsheet 20 are then passed through rollers 250 which direct the webs into face-to-face contact with each other. The liquid-permeable topsheet 30 and the secondary topsheet 20 exit the rollers 250 in a laminated condition as the composite web 70. The composite web 70 is then directed to a printing unit 204 which delivers a volume of ink 206 (preferably, but not necessarily, this constitutes the total volume of ink applied) to the second surface 20B of the secondary topsheet 20. The composite web 70 can be pulled across an idler positioned at the printing unit 204 such that ink 206 is applied to the composite web 70 at any point between perpendicular (e.g., directly above the idler) to the tangent, or 90 degrees from perpendicular. This is done to reduce ink blow-through through the composite web 70 and improve image quality. The composite web 70 can then be directed past an adhesive coater 208 to prepare the composite web 70 for joining with the top core 22 (or core 90), which can be provided on a storage roll, as illustrated. In an alternative process 175, as shown in FIG. 7, the secondary topsheet 20 and the liquid-permeable topsheet 30 are fusion bonded with rollers 260 to form the composite web 70. Also, the printing unit 204 is positioned to apply the volume of ink 206 at an angle (shown as print angle θ) relative to a position perpendicular (in this case, vertical) to the composite web 70. The print angle θ can be within the range of about 0 degrees to about 30 degrees, for example, where a 0-degree print angle is perpendicular to the composite web 70. In other embodiments, the process 150 can be rotated/oriented 360 degrees such that the printing unit 204 prints upwards, sideways, etc. versus downward as depicted. For instance, the printing unit 204 may be oriented at 270 degrees (printing upwards against gravity), however, more reliability issues due to ink and dust falling back onto the printer may occur.

In some embodiments, the ink delivered to the composite web 70 by the printing unit 204 can be in the form of ink drops. One ink deposit 50 may comprise multiple ink drops. The volume of the ink drops can depend on the particular printing technology. By way of example, printing units that are VIDEOJET continuous ink jet printers can have ink drop volumes of about 240 pL and are delivered at relatively high drop velocities (e.g., about 13 m/s). Other printing technology (e.g., piezo drop on demand) can deliver ink drops having relatively small volumes, such as ink drops having a volume ranging from about 1 pL to about 24 pL, that are delivered at lower drop velocities (i.e., about ½ m/s) than continuous inkjet printing. Those skilled in the art know there are different inkjet technologies (e.g., continuous, piezo, thermal, valve) and different drop size ranges and different jet velocities. But, pertaining to printing to a composite web to (1) improve image quality and (2) minimize line hygiene issues (ink blow-through), this is how drop size and drop velocity are related. Smaller drop size infers that the CD dpi (resolution) is higher. The range 1-24 pL would equate to a CD resolution of 300-600 dpi. The VIDEOJET CD resolution is 128 dpi. So, more drops in CD means better opportunity to hit a fiber, which results in better image quality and less ink blow-though. The slower the drop speed, the less ink blow-through. The smaller drops will be slower due to mass alone.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A process of printing on a composite web, comprising the steps of:
   providing a nonwoven layer;
   providing a second layer comprising a nonwoven web, an apertured film, or a combination thereof;
   combining the nonwoven layer with the second layer to define the composite web; and
   applying a volume of ink to the composite web, wherein a first portion of the volume of ink is associated with the nonwoven layer and a second portion of the volume of ink is associated with the second layer, and wherein the step of applying the volume of ink comprises blowing a portion of the volume of ink through the composite web, wherein the blow-through portion of the volume of ink is less than about 10 percent of the volume of ink.

2. The process of claim 1, wherein the nonwoven layer is a secondary topsheet and the second layer is a topsheet.

3. The process of claim 1, wherein combining the nonwoven layer with the second layer comprises a method selected from a group consisting of fusion bonding, gluing, gluing-and-embossing, and combinations thereof.

4. The process of claim 1, wherein the composite web has a first surface and an opposing second surface; wherein the volume of ink is applied to the second surface of the composite web; wherein the composite web is combined with an absorbent core and a liquid impermeable layer to form an absorbent article; and wherein the second surface of the composite web faces the absorbent core.

5. The process of claim 1, wherein the composite web is combined with an absorbent core and a liquid impermeable layer to form an absorbent article, wherein the volume of ink is at least partially visible as a visual signal when viewing an outer surface of the absorbent article, and wherein the outer surface is at least partially defined by the second layer.

6. The process of claim 1, wherein the second layer has an air permeability of at least about 300 cubic ft. per minute (cfm) per sq. ft.

7. The process of claim 1, wherein the first portion is about 30% to about 90% of the volume of ink and the second portion is about 10% to about 70% of the volume of ink.

8. The process of claim 1, wherein the second layer comprises an apertured film.

9. The process of claim 1, wherein the second layer comprises a nonwoven material.

10. The process of claim 1, wherein the second layer comprises a combination of film and nonwoven materials.

11. The process of claim 2, wherein the secondary topsheet has a basis weight of between about 10 gsm to about 55 gsm.

* * * * *